United States Patent [19]

Guastavino

[11] 4,402,215
[45] Sep. 6, 1983

[54] RHEOLOGICAL TESTING METHOD

[75] Inventor: Thomas G. Guastavino, Cherry Hill, N.J.

[73] Assignee: The United States of America, Washington, D.C.

[21] Appl. No.: 301,254

[22] Filed: Sep. 11, 1981

[51] Int. Cl.³ ............................................ G01N 11/04
[52] U.S. Cl. ........................................................ 73/55
[58] Field of Search ........................................ 73/55, 56

[56] References Cited

U.S. PATENT DOCUMENTS 3,048,030  8/1962  De Haven ............................. 73/56
3,720,097  3/1973  Kron ..................................... 73/55

FOREIGN PATENT DOCUMENTS 811104  3/1981  U.S.S.R. ............................... 73/55

Primary Examiner—E. R. Kazenske
Assistant Examiner—Joseph W. Roskos
Attorney, Agent, or Firm—Otto M. Wildensteiner; Harold P. Deeley, Jr.

[57] ABSTRACT

A method of testing the potential anti-misting and/or the drag reducing properties of a polymer modified fluid by testing its rheological behavior under increasing pressure. It has been found that the quantity of such fluids that can be pumped through a given system decreases as the pumping pressure is increased, thus giving an indication of the presence of the desired properties.

2 Claims, 5 Drawing Figures

RHEOLOGICAL TESTING METHOD

STATEMENT OF GOVERNMENT INTEREST

The present invention was made by a Government employee and may be made and used by or for the Government of the United States for governmental purposes without the payment of any royalties thereon or therefor.

BACKGROUND

Aircraft gas turbine engines operate on fuel which is basically kerosene, which is much less volatile than gasoline. However, it has been found that in the event of a crash the fuel is subjected to a shock which causes it to spray out of the tank in a highly flammable mist; this is the cause of most of the post-crash fires, which are the cause of more deaths and injuries than the crashes themselves. Likewise, if the tank is ruptured in flight the fuel gets caught in the airstream and is broken up into the same highly flammable mist.

To combat this misting tendency, certain additives have been discovered which can be added to the fuel to reduce its mist formation under these conditions; these are known as "anti-misting" additives. See U.S. Pat. No. 3,996,023 for a discussion of anti-misting polymer additives. It has been found that these same polymers, when dissolved in fluids, reduce the friction generated when the mixture is flowing in a pipeline or over a surface; see U.S. Pat. No. 3,692,676.

Although the desirable properties of these modified fluids are well known, a good test has not yet been devised which will measure these properties or which will allow the prediction of these properties when an unknown additive is tested for the first time. The prior art shows two tests, neither of which is very exact or which produces easily quantifiable results. The first of these tests is that described in U.S. Pat. No. 3,996,023 and comprises dropping a thin stream of fluid into the center of a hollow cylinder whose walls are lined with absorbent paper; the drops of fluid which splash onto the paper are then counted, and the polymer additive concentration is increased until no drops splash onto the paper. The second test is described in U.S. Pat. No. 3,998,605 and is essentially a version of the "slump" test that is used to determine the water content of freshly-mixed concrete. In this test the liquid under test is placed in an open ended cylinder 20 cm in diameter and 20 cm high and allowed to stand for a short time. The cylinder is then lifted up, and the behavior of the liquid is observed. If the fluid spreads out to a thickness of less than a millimeter, the concentration of additive is too low; if it spreads out to a thickness of 10 cm or more, the concentration is too high for present fuel systems (i.e., it would not flow out of the fuel tanks, special pumps would be required, etc.). Under this test the optimum thickness is 0.5–5 cm.

The present invention is a test which is clean, easily performed, and produces useful results.

OBJECTS OF THE INVENTION

Accordingly, it is an object of the present invention to provide a method of determining the potential anti-misting properties of a polymer additive.

It is a further object of the present invention to provide such a test having a numerically quantifiable result.

It is a further object of the present invention to provide such a test which requires only commercially available equipment.

It is a further object of the present invention to provide such a test wherein the results of the test can be displayed graphically.

SUMMARY

Briefly, the present invention is a method of determining the potential anti-misting behavior of a polymer modified fluid by pumping the fluid through a section of tubing and measuring the flow per unit time. It has been found that when the fluid contains the proper concentration of a polymer which imparts the desired properties, the flow rate per unit time decreases as the pumping pressure is increased. A graph of the flow versus pressure characteristics of the fluid clearly shows the influence of the polymer, and indicates its potential anti-misting ability.

DESCRIPTION OF THE PREFERRED EMBODIMENT

Figure 1:
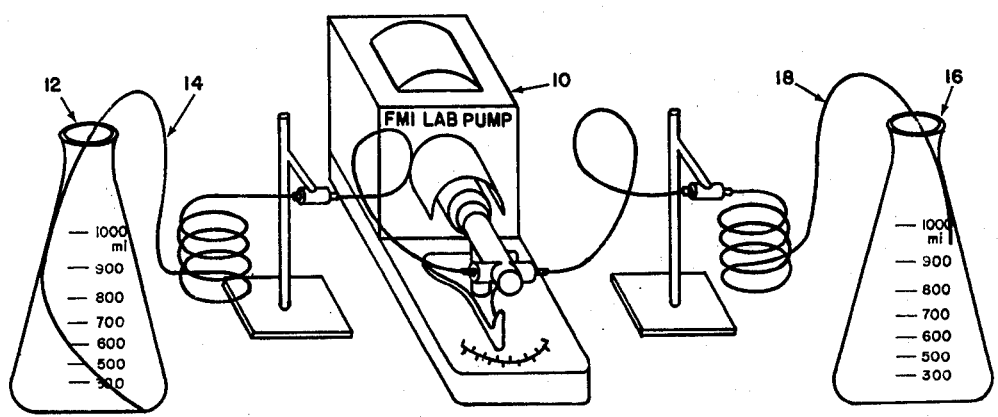
FIG. 1 shows the overall test setup.

FIG. 1 shows the equipment required for making the tests to determine the anit-misting behavior. The primary piece of equipment is the FMI Lab Pump 10, manufactured by Fluid Metering, Inc., 29 Orchard Street, Oyster Bay, N.Y. 11771; for all but the strictural acceleration test (FIG. 5) the pump was Model RP-G400; for the strictural acceleration test of FIG. 5 it was Model RP-G150 pump. As is well known in the art, this is a pump whose stroke length, and consequently output per stroke, can be varied from 0 to 100 percent of maximum. Pump 10 takes liquid from flask 12 through inlet line 14 and transfers it to flask 16 through outlet line 18. Inlet line 14 has 3¾ turns of 3 inches diameter in it, and outlet line 18 has 4 turns of 3 inches diameter in it. Both inlet 14 and outlet line 18 are of ⅛ inch diameter stainless steel tubing; inlet line 14 is 186 cm long, and outlet line 18 is 315 cm long.

The test is designed to measure the anit-misting properties of known additives when mixed with aviation kerosene; some examples are ter acrylic polymer, polyisobutylene, isotactic polyethylene-polypropylene, and butadiene-styrene. See U.S. Pat. No. 3,996,023 for a discussion of aviation kerosene and anti-misting polymers in general.

The prior art has recognized the property that applicant has found a way to measure. A solution of polymer in kerosene, in an amount sufficient to produce the desired anti-misting behavior without making the kerosene too jelled to flow readily, when shaken in a flask forms a gel on the walls of the flask that disappears after a few seconds. This is the phenomenon termed "early turbulence" by others, which gives rise to the test described in U.S. Pat. No. 3,998,605 wherein a stream of anti-misting kerosene is dropped from a certain height and the amount of droplet formation is measured, the number of droplets being inversely proportional to the amount of polymer in the kerosene.

In applicant's test, the fuel being tested is pumped from flask 12 into flask 16 and the amount of fluid pumped in a certain time is measured. It was found that it took 188.4 seconds to pump 750 ml of unmodified Jet A fuel when the pump was set at 100 percent stroke, hence these figures were taken as the baseline. In all future tests, the time required to pump 750 ml of polymer modified fuel at a given pump setting (i.e., percent of stroke) was measured, and then the quantity was referenced to 188.4 seconds by multiplying 750 ml by the ratio of 188.4 seconds divided by actual time in seconds. This produces a graph of quantity of fuel pumped in 188.4 seconds at any pump setting of 0 to 100 percent stroke.

Unless specified otherwise, all figures show the performance of 0.30 percent by weight FM 9 polymer added to Jet A aviation fuel. "FM 9" is the name given by Imperial Chemical Industries, Ltd. to its ter acrylic polymer which is the polymer on which most anti-misting work has been done. See European Patent Application No. 16,535 for a description of the polymer and how it is made.

A comparison of the figures will reveal that there are differences in the data points between tests that were run at the same conditions. This is because FM 9 is a substance which has a certain range of properties, such as molecular weight, rather than a definite one (see European Patent Application No. 16,535). Jet A fuel likewise has a range of properties, since it is a mixture of hydrocarbons, rather than a set of definite properties. Thus the variation in the properties of Jet A, added to the variation in the properties of FM 9, results in what would ordinarily be unacceptably large variations in the resulting data points. A similar variation would presumably result from the use of the other polymers, since they also have a range of properties such as molecular weight.

Although the figures show flow rates plotted as a function of pump setting, it is obvious that pump output pressure increases as pump setting is increased because the only way that more fluid can be pumped through a tube is to increase the pumping pressure. Therefore, the figures also show the variation in flow rate with pressure and can easily be converted from pump setting to pressure.

Figure 2:
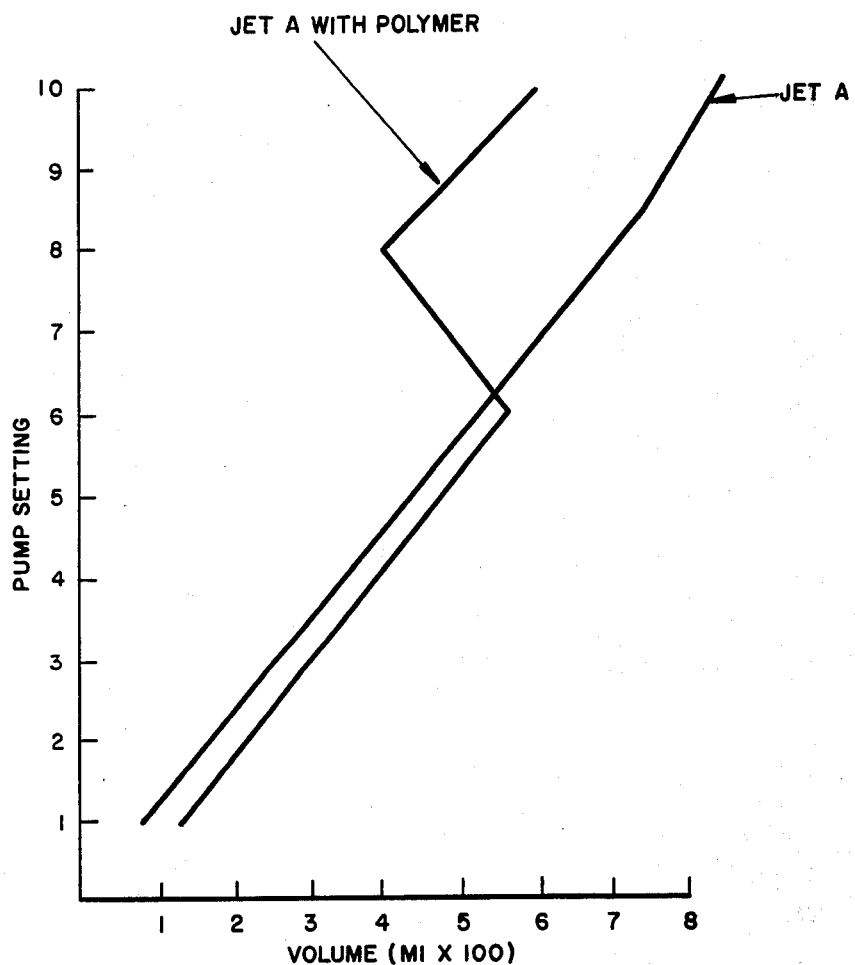
FIG. 2 shows the behavior of straight Jet A fuel and Jet A fuel with a polymer additive.

FIG. 2 shows a graph of unmodified Jet A fuel compared to a graph of Jet A with 0.30 percent ter acrylic polymer added to it. This concentration has been previously determined to provide good anti-misting properties; as can be seen, it also shows a surprising reversal in pump output at pump setting 6. The reason for this reversal is not definitely known; however, it is a function of the same properties which produce the anti-misting behavior, hence it is a quantifiable indicator of that performance. Along with the flow reversal, there is a cloudiness in the output flask that is the result of the gellation phenomenon referred to earlier. This cloudiness disappears after a few seconds, just as the gel does. A comparison of the results shown in FIG. 2 with the same type of test performed on four standard viscosity liquids (silicone oils) indicates an approximate doubling of the viscosity at the point of the onset of the flow reversal. However, this is to be expected in light of the observed phenomena such as cloudiness and gel formation, reversal in output, etc.

Figure 3:
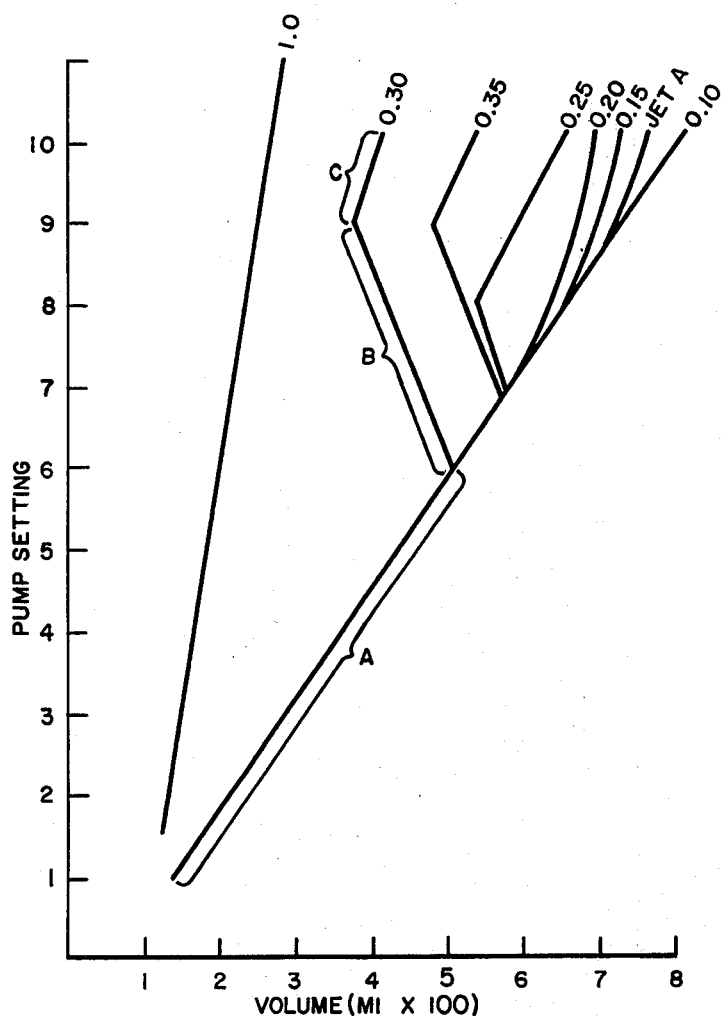
FIG. 3 shows the effects of polymer concentration on behavior.

FIG. 3 shows the effect of polymer concentration on flow. As can be seen, there is a slight increase in flow at a concentration of 0.1 percent by weight. This is probably due to the fact that all of these polymers are useful as friction-reducing additives in this concentration range (see U.S. Pat. No. 3,692,676 for a discussion of the friction-reducing properties of these polymers). As the concentration of polymer is increased, the quantity of fluid pumped at the higher pump settings decreases; note that the onset of the decrease occurs at lower and lower pump settings. Somewhere between 0.20 and 0.25 percent the quantity shows an actual decrease, at pump setting 7. As the concentration of polymer is increased further, the decrease in quantity pumped becomes more pronounced and the onset of the decrease occurs at lower pump settings. At a point somewhat above 0.3 percent the flow changes again, this time showing a decrease in the previous behavior—i.e., the quantity of fluid pumped at a given pump setting starts to increase, and the onset of the decrease occurs at a higher pump setting. Above 0.35 percent polymer the flow again changes, this time showing a straight line. This is because at these higher polymer concentrations the flow is entirely in the range that exists in the lower concentrations at the higher pump settings. That is, at additive concentrations of 0.35 and below the fluid may be thought of as having 3 types of internal structure; pure liquid, wherein an increase in pump setting produces an increase in volume pumped; a range wherein the amount of what other researchers have called early turbulence increases with increasing pump settings and the amount pumped decreases with increasing pump settings; and a range wherein the formation of early turbulence occurs at all pump settings and the mixture behaves like a thick liquid, with an increase in pump setting producing a small increase in amount pumped. These are exemplified by the three portions of the curve for 0.30 percent concentration in FIG. 3 labelled A, B, and C respectively.

The important thing is not at what pump settings these changes occur, but the fact that they occur at all and that using applicant's test they can be measured. Since the phenomenon of early turbulence has been reported only in connection with the addition of friction reducing and anti-misting polymers, it is safe to assume that no other fluids exhibit it. Therefore the significance of applicant's test is that it provides a quick, neat, and easily quantifiable test to determine the presence of the desirable properties.

Figure 4:
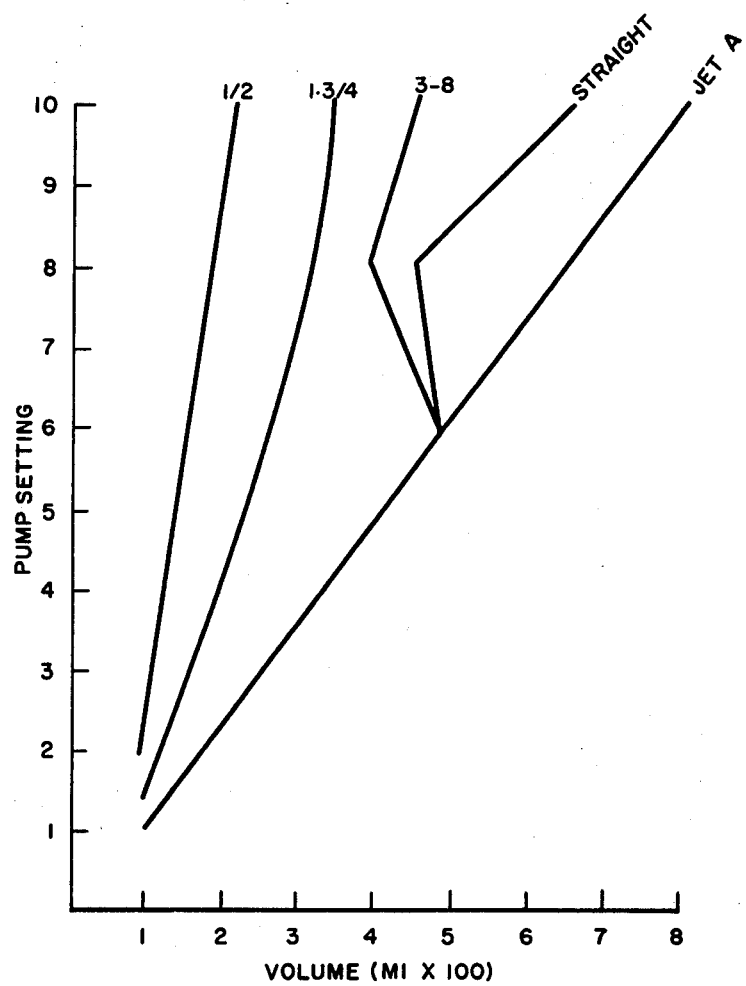
FIG. 4 shows the effect of coil diameter on behavior.

FIG. 4 shows the effects of centrifugal acceleration on the flow characteristics. For this test the setup shown in FIG. 1 was modified by changing the diameter of the coils shown in the outlet tubing; the polymer concentration was held constant at 0.30 percent. With no coils in the tubing the output was as shown by the curve labeled "straight." When the tubing was coiled, the fluid was forced to undergo greater and greater centrifugal accelerations as the coil diameters were decreased. At some point between coil diameters of 3 inches and 1¾ inches the fluid exhibited fully developed early turbulence, and behaved like a thick liquid. This is analogous to the situation shown in FIG. 3 wherein the concentration was raised to the point where the early turbulence was developed at all pump settings. Thus it appears that the mechanism which produces the early turbulence is responsive to the centrifugal accelerations undergone by the fluid, and any comparison testing should be done with a single physical setup so as to eliminate extraneous effects.

Figure 5:
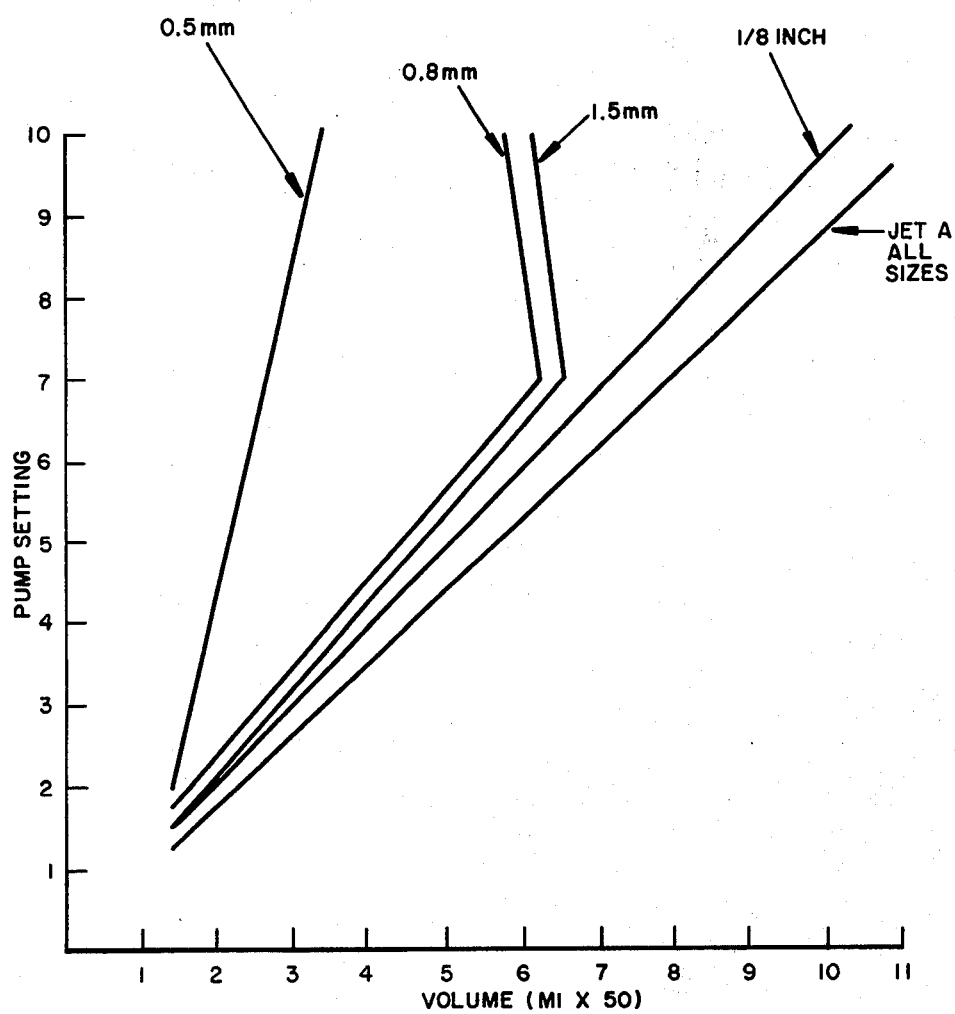
FIG. 5 shows the effect of tubing diameter on behavior.

FIG. 5 shows the effects of strictural acceleration on flow. In this test the tubing diameters were reduced to the sizes shown. It was found that at the smaller diameters used for these tests the output of the original pump was too high and the polymer was rendered insoluble in the Jet A fuel; for this reason a smaller pump, the Model RP-G150, was used. In addition, the tubing length was changed to 150 cm for both the inlet and outlet tubing, with one large loop in each. As can be seen, the output of unmodified Jet A is the same for all diameters while the output of the polymer-modified fuel decreases with decreasing tubing size. The curves labelled 1.5 and 0.8 mm show a decrease in flow which starts at pump setting 7, the same as the other curves; the fact that these curves do not show an increase in flow at a higher setting is due probably because that second reversal point is outside of the parameters of the present test setup. At the smallest tube diameter, 0.5 mm, the fluid had fully developed early turbulence at all pump settings and behaved like a thick liquid. This test shows that forcing the fluid through a smaller tube, to produce a linear acceleration, has the same effect on it as any of the other accelerations.

What is claimed is:

1. The method of measuring the potential anti-misting behavior of a polymer-modified fluid, which comprises:
   a. adding a polymer to said fluid;
   b. pumping said fluid and polymer through a conduit at a first pressure;
   c. measuring the flow rate at said first pressure;
   d. increasing the pumping pressure applied to said fluid and polymer and measuring the flow rate at the increased pumping pressure; and
   e. comparing the flow rate at a given pumping pressure with the flow rate at a lower pumping pressure to determine if the flow rate decreases with increasing pumping pressure.

2. The method of claim 1 further including making a graph of flow rate versus pumping pressure for said fluid.

* * * * *